United States Patent
Yamamoto et al.

(10) Patent No.: US 11,992,460 B2
(45) Date of Patent: May 28, 2024

(54) ADAPTER AND INJECTION FLUID TRANSFER METHOD

(71) Applicant: DAICEL CORPORATION, Osaka (JP)

(72) Inventors: Yuzo Yamamoto, Tokyo (JP); Takamasa Suzuki, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 538 days.

(21) Appl. No.: 17/282,721

(22) PCT Filed: Oct. 3, 2019

(86) PCT No.: PCT/JP2019/039195
§ 371 (c)(1),
(2) Date: Apr. 2, 2021

(87) PCT Pub. No.: WO2020/071506
PCT Pub. Date: Apr. 9, 2020

(65) Prior Publication Data
US 2022/0000717 A1   Jan. 6, 2022

(30) Foreign Application Priority Data
Oct. 4, 2018 (JP) .................................. 2018-189392

(51) Int. Cl.
*A61J 1/20* (2006.01)
(52) U.S. Cl.
CPC .................................. *A61J 1/2048* (2015.05)
(58) Field of Classification Search
CPC .......... A61J 1/2096; A61J 1/2048; A61M 5/30
See application file for complete search history.

(56) References Cited

U.S. PATENT DOCUMENTS 4,338,980 A * 7/1982 Schwebel ............ A61M 5/1782
141/369
6,174,304 B1 * 1/2001 Weston ................. A61J 1/2096
604/82
(Continued)

FOREIGN PATENT DOCUMENTS

| WO | WO 01/52920 A2 | 7/2001 | |
| WO | WO-0152920 A2 * | 7/2001 | ............ A61J 1/2096 |
| WO | WO 2008/103997 A2 | 8/2008 | |

OTHER PUBLICATIONS

Extended European Search Report for European Application No. 19869157.8, dated Jul. 22, 2022.
(Continued)

*Primary Examiner* — Timothy P. Kelly
(74) *Attorney, Agent, or Firm* — Birch, Stewart, Kolasch & Birch, LLP (57) ABSTRACT

The adapter includes a housing and a filling nozzle provided in communication with a containing portion in the housing and coming into contact with an end surface of the injection device, in which the injection port of the injection nozzle is formed, when the housing is attached to the injection device. An open end of the filling nozzle is set to be smaller than an inner diameter of the containing portion and larger than the injection port. Of an internal space of the housing from a partial region of the containing portion to the open end, at least a predetermined space being continuous and including the partial region is formed in a manner where an inner diameter of the predetermined space decreases toward a side of the open end. According to this configuration, the injection fluid can be suitably transferred from the outside to a needleless injector.

8 Claims, 8 Drawing Sheets

(56) References Cited

U.S. PATENT DOCUMENTS

| | | |
|---|---|---|
| 6,223,786 B1 | 5/2001 | Castellano |
| 7,059,368 B2 * | 6/2006 | Filler .................... A61B 50/20 604/416 |
| 2002/0161334 A1 | 10/2002 | Castellano et al. |

OTHER PUBLICATIONS

International Search Report for International Application No. PCT/JP2019/039195, dated Dec. 24, 2019, with English translation.
Written Opinon of the International Searching Authority for International Application No. PCT/JP2019/039195, dated Dec. 24, 2019, with English translation.

* cited by examiner

ADAPTER AND INJECTION FLUID TRANSFER METHOD

TECHNICAL FIELD

The present invention relates to an adapter for transferring an injection fluid from outside to an injector side, and an injection fluid transfer method using the adapter.

BACKGROUND ART

An injector can be exemplified by a needleless injector as a device that injects a liquid medicine or the like into a target region of an organism or the like. In recent years, a needleless injector that does not include an injection needle has been developed in view of ease of handling, sanitation, and the like. In general, a needleless injector has been brought into practical application that has a configuration in which a liquid medicine pressurized by a driving source such as compressed gas or a spring is injected toward a target region, and the liquid medicine is injected into the inside of the target region through use of the kinetic energy of the liquid medicine. Since there is no mechanical configuration (the injection needle, for example) forming an injection fluid flow path in such a needleless injector, in a preparatory stage for using the device, it is necessary to pay commensurate attention to transferring the injection fluid to the needleless injector in a sanitary manner.

Here, in Patent Document 1, a configuration is disclosed in which a needleless injector and a vessel are coupled using a coupling device and an injection fluid is transferred. The needleless injector is attached to one side of the coupling device, and the vessel is attached to the other side of the coupling device. The vessel contains the injection fluid to be injected by the needleless injector. Then, a contact surface of the coupling device is shaped in a manner corresponding to a distal end surface of the needleless injector, and an orifice of the coupling device is in a state of facing an orifice on the needleless injector side. Further, when transferring the injection fluid from the vessel to the needleless injector, the contact surface of the coupling device is formed such that the injection fluid does not adhere to the distal end surface of the needleless injector, thus suppressing the occurrence of bacteria or the like.

CITATION LIST

Patent Document

Patent Document 1: US 2002/0161334 A

SUMMARY OF INVENTION

Technical Problem

In known technology, a diameter of an orifice at a distal end portion of a coupling device is formed to be smaller than a diameter of an orifice of a nozzle portion of a needleless injector, and, during transfer of an injection fluid, the injection fluid does not come into contact with a distal end surface of the needleless injector (thus preventing bacteria and the like from propagating on the distal end surface of the needleless injector). Generally, the needleless injector exerts a high pressure on the injection fluid and uses that energy to inject the injection fluid toward a target region, and thus, an orifice diameter for that injection is very small. Thus, in known art, the orifice diameter on the coupling device side becomes smaller than the orifice diameter on the needleless injector side, and when attempting to transfer the injection fluid using the coupling device, a relatively long time is needed for that transfer. Further, in a case of transferring a very small amount of injection fluid, since the injection fluid is configured as not being easily transferred to the distal end of the orifice of the coupling device, air present in the surroundings is also taken in and transferred to the needleless injector.

In light of the problem described above, an object of the present invention is to provide a technique that makes it possible to suitably transfer an injection fluid from outside to a needleless injector.

Solution to Problem

In order to solve the above problem, the present invention employs a configuration in which, as well as an open end of an adapter being configured to be smaller than an inner diameter of a containing portion and to be larger than an injection port of an injection nozzle of an injection device, a predetermined space whose diameter continuously decreases is disposed in the interior of the adapter, and thus, at a time of transfer, a space where the injection fluid disperses is not present. With such a configuration, it is possible to transfer the injection fluid from the outside to the injection device via the adapter in a hygienic and quick manner. Further, it is possible to suppress unintentional mixing of the injection fluid and air at the time of the transfer.

Specifically, the present invention is an adapter for transferring a predetermined injection fluid, via an injection port of an injection nozzle, to an injection device that injects the predetermined injection fluid from the injection nozzle. The adapter includes: a housing defining a containing portion containing the predetermined injection fluid to be transferred, the housing being configured to be attachable to and detachable from the injection device; and a filling nozzle provided in communication with the containing portion in the housing, when the housing is attached to the injection device, the filling nozzle being configured to come into contact with an end surface of the injection device, in which the injection port of the injection nozzle is formed, the filling nozzle being configured to allow the predetermined injection fluid contained in the containing portion to flow to a side of the injection nozzle, an open end of the filling nozzle being set to be smaller than an inner diameter of the containing portion and larger than the injection port of the injection nozzle. Then, of an internal space of the housing from a partial region of the containing portion to the open end of the filling nozzle, at least a predetermined space being continuous and including the partial region is formed in a manner where an inner diameter of the predetermined space decreases toward a side of the open end of the filling nozzle.

The above-described injection device is a device that injects the injection fluid from the injection nozzle to the outside, but as a preparatory stage for the injection, it is necessary to transfer the injection fluid from the outside via the injection port of the injection nozzle. The adapter of the present invention is used in such a transfer of the injection fluid to the injection device. At this time, the adapter may be attached to the injection device itself, or, as an alternative method, may be attached to a component constituting the injection device. In the present invention, an adapter having a configuration where the adapter is attached to the component is also understood to be the adapter that is attached to the injection device, as long as the component constitutes a part of the injection device. Note that, in the present application, in terms of the injection of the injection fluid, the injection device is not limited to a particular mode. For example, energy used for pressurizing the injection fluid transferred via the adapter in order to perform the injection may be chemically-generated energy, or may be combustion energy generated by an oxidation reaction of a low explosive, a high explosive, or the like. Further, as another method, the energy for pressurizing may be generated electrically. As one example, energy caused by a piezoelectric element or an electromagnetic actuator driven by applied electric power may be employed. Further, as yet another method, the energy for pressurizing may be generated physically. As one example, elastic energy of an elastic body or internal energy of a compressed body, such as compressed gas, may be employed. Further, the energy for pressurizing may be a composite-type energy obtained by appropriately combining the above-described combustion energy, energy generated by electric power, and internal energy such as the elastic energy.

Further, in the present invention, the injection fluid transferred to the injection device via the adapter can be exemplified by a substance including a component expected to have an effect in the target region or a component expected to exert a predetermined function in the target region. Thus, as long as at least the injection is possible, with respect to a physical form of the injection fluid, the injection fluid may be present in a state of being dissolved in a liquid, or may be in a state of simply being mixed, without being dissolved, in a liquid. As one example, a predetermined substance to be administered includes vaccine for increasing antibodies, a protein for cosmetic enhancement, a cultured cell for hair regeneration, and the like, and the injection fluid is formed by including these in a liquid medium in an injectable manner. Note that, the medium is preferably a medium that does not hinder the above-described effect and function of the predetermined substance in a state of being injected inside the target region. As another method, the medium may be a medium that exerts the above-described effect and function by acting together with the predetermined substance in the state of being injected inside the target region.

Since the injection fluid is administered into the target region in this way, it is necessary to take care, in terms of hygiene, when transferring the injection fluid to the injection device from the containing portion defined in the housing of the adapter. In particular, when the transfer requires a long time period, a time period over which the injection fluid is exposed to the external environment becomes longer, which is not preferable in terms of hygiene. When the housing of the adapter is attached to the injection device for the transfer of the injection fluid, the above-described adapter is formed in a state where the transfer of the injection fluid is possible in a state where the filling nozzle is in contact with the end surface of the injection nozzle of the injection device. Then, the open end of the filling nozzle is set to be smaller than the inner diameter of the containing portion and to be larger than the injection port of the injection nozzle. As a result, the filling nozzle diameter through which the injection fluid flows does not become unnecessarily small, and it is possible to avoid a situation where a transfer speed of the injection fluid significantly deteriorates and the transfer time becomes longer. Further, at the time of the transfer, the filling nozzle is in contact with the end surface of the injection device, and the adapter can be stably positioned with respect to the injection device, and thus, the suitable transfer of the injection fluid can be achieved.

Further, in the course of transferring the injection fluid from the containing portion to the injection device, the injection fluid moves from the partial region of the containing portion, through the internal space of the filling nozzle, and toward the open end of the filling nozzle. Here, in the above-described adapter, the continuous predetermined space including at least the partial region of the adapter is formed in the manner where the inner diameter of the predetermined space decreases toward the side of the open end of the filling nozzle. According to such a configuration, at the time of the transfer, the injection fluid is less likely to be dispersed inside the filling nozzle and is more easily collected, and thus, at the time of the transfer, it is possible to suppress ambient air from being included and being transferred to the injection device. According to the adapter of the present application, it is possible to suitably transfer the injection fluid from the outside to a needleless injector. Then, more preferably, the predetermined space may be a space that includes all of the internal space of the partial region and the filling nozzle. In this case, from the partial region to the open end of the filling nozzle, the predetermined space may be formed in a manner where the inner diameter of the predetermined space decreases continuously toward the side of the open end of the filling nozzle. According to this configuration, the dispersion of the injection fluid at the filling nozzle can be more effectively suppressed, and even when a very small amount of the injection fluid is transported, the mixing with air can be effectively suppressed.

Further, in the above-described adapter, the filling nozzle may include a protruding portion having an annular shape and protruding from the filling nozzle toward a distal end side of the adapter, the protruding portion being formed in a manner where, when the housing is attached to the injection device, a distal end of the protruding portion comes into contact with the end surface of the injection device. As a result of the above-described adapter having such a protruding portion, the annular protruding portion comes into contact with the end surface of the injection device while surrounding a portion at which the filling nozzle and the injection nozzle are in communication with each other. As a result, the adapter can be more stably positioned with respect to the injection device at the time of the transfer of the injection fluid, the injection fluid is inhibited from leaking out, and the transfer to the injection device is more favorably achieved.

Further, the protruding portion may be formed of a flexible member. According to such a configuration, the protruding portion suitably deforms when the adapter is positioned with respect to the injection device, and a suitable contact state is thus formed between the adapter and the injection device. In this way, a suitable sealing performance is created between the adapter and the injection device, and thus the injection fluid can be inhibited from leaking at the time of the transfer, and more of the injection fluid can be transferred to the injection device. Note that the flexible member forming the protruding portion is not necessarily limited to a particular material, and a suitable flexible material can be selected from the perspective of the sealing performance effective for the transfer of the injection fluid.

Here, with respect to the above-described adapter, the injection device may include a nozzle portion having a cylindrical shape and internally including the injection nozzle, the nozzle portion being formed exposing the injection port of the injection nozzle at an end surface of the nozzle portion. Based on this, the housing may include a first cylindrical portion provided surrounding the filling nozzle, in the housing, the first cylindrical portion being in a fitted state with an outer peripheral wall surface of the nozzle portion when the housing is attached to the injection device. By employing such a configuration, when the adapter is attached to the injection device via the housing, the first cylindrical portion is in a positional relationship of contacting and supporting the outer peripheral wall surface of the nozzle portion, and thus the stability of an attached state can be increased.

Further, in the adapter having the above-described configuration, the outer peripheral wall surface of the nozzle portion may form a tapered surface inclined along an axial direction of the nozzle portion. In this case, when the housing is attached to the device main body, an inner wall surface of the first cylindrical portion may be in the fitted state while pressing the outer peripheral wall surface of the nozzle portion. As a result, the contact and support between the inner wall surface of the first cylindrical portion and the outer peripheral wall surface of the nozzle portion is strengthened, and thus, the more stable attachment of the adapter can be expected.

Further, the above-described adapter may further include a holding portion configured to hold the fitted state between the first cylindrical portion and the outer peripheral wall surface of the nozzle portion when the housing is attached to the injection device. The holding portion holds a coupled state between the first cylindrical portion and the outer peripheral wall surface of the nozzle portion, and thus, the transfer of the injection fluid can be more favorably performed.

From the perspective of improving the stability of the positioning between the adapter and the injection device, the housing may include a second cylindrical portion provided surrounding the first cylindrical portion, in the housing, the second cylindrical portion being in a fitted state with an outer peripheral wall surface of the injection device when the housing is attached to the injection device. By employing such a configuration, the adapter can be positioned with respect to the injection device via both the contact between the first cylindrical portion and the nozzle portion, and the contact between the second cylindrical portion and the injection device. As a result, the stability of the attached state of the adapter further increases, and the transfer of the injection fluid can be more favorably performed.

Further, the invention of the present application can also be understood from an aspect of an injection fluid transfer method to an injection device from an adapter in which an injection fluid is contained in a containing portion. Specifically, the method includes preparing an adapter for transferring a predetermined injection fluid, via an injection port of an injection nozzle, to an injection device that injects the predetermined injection fluid from the injection nozzle, the adapter including a housing defining a containing portion containing the predetermined injection fluid to be transferred and a filling nozzle connected to the containing portion in the housing, an open end of the filling nozzle being set to be smaller than an inner diameter of the containing portion and larger than the injection port of the injection nozzle, of an internal space of the housing from a partial region of the containing portion connected to the filling nozzle to the open end of the filling nozzle, at least a predetermined space being continuous and including the partial region being formed in a manner where an inner diameter of the predetermined space decreases toward a side of the open end of the filling nozzle. The method includes attaching the housing to the injection device and causing a distal end of the filling nozzle to be in contact with an end surface of the injection device, in which the injection port of the injection nozzle is formed, pouring the predetermined injection fluid into the containing portion, and transferring the predetermined injection fluid from the containing portion to the injection device in a state where the adapter is positioned above the injection device in a vertical direction. Further, the technical concepts disclosed in relation to the above-described adapter are applicable to the invention relating to the above-described transfer method insofar as no technical inconsistency arises.

Advantageous Effects of Invention

The present invention makes it possible to suitably transfer an injection fluid from the outside to a needleless injector.

DESCRIPTION OF EMBODIMENTS

An adapter 90 used for the transfer of the injection fluid in a needleless injector (hereinafter simply referred to as "injector") 1 according to an embodiment of the invention of the present application will be described below with reference to the drawings. The injector 1 is a needleless injector that injects an injection fluid, which corresponds to an injection intended substance of the present application, into a target region, using combustion energy of an explosive. In other words, the injector 1 is a device that injects the injection fluid into the target region without using an injection needle. The injector 1 will be described prior to describing details of the adapter 90.

Figure 4:
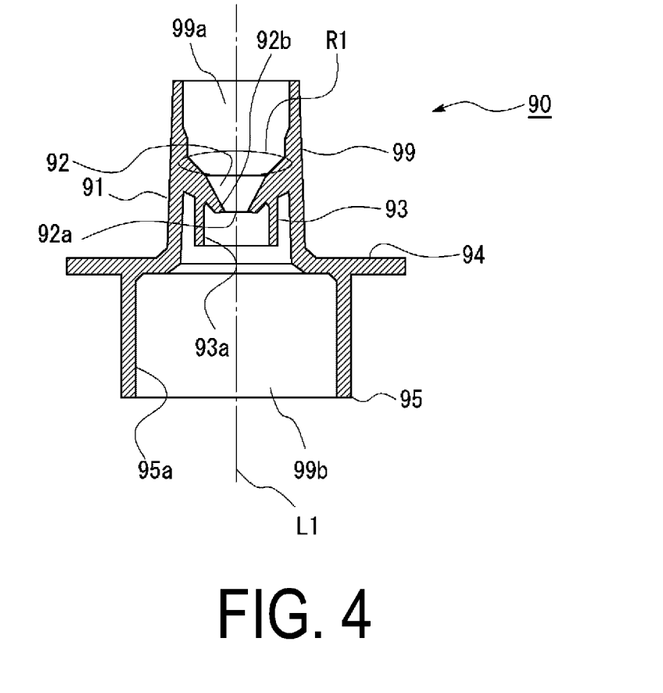
FIG. 4 is a cross-sectional view of the adapter illustrated in FIG. 3.

Note that, configurations of the following embodiment are provided as examples, and the invention of the present application is not limited to the configurations of the embodiment. Note that, in the present embodiment, as terms indicating a relative positional relationship in a longitudinal direction of the injector 1, "distal end side" and "base end side" are used. "Distal end side" indicates a side close to the distal end of the injector 1 to be described later, that is, a position close to an injection port 31a, and "base end side" indicates a direction opposite to the "distal end side" in the longitudinal direction of the injector 1, that is, a direction toward a side of a drive portion 7. Further, in the adapter 90, a downstream side of a flow during transfer of the injection fluid, that is, the lower side illustrated in FIG. 4, is the "distal end side, and the opposite side thereto, that is, the upper side illustrated in FIG. 4, is the "base end side".

Configuration of Injector 1

Figure 1:
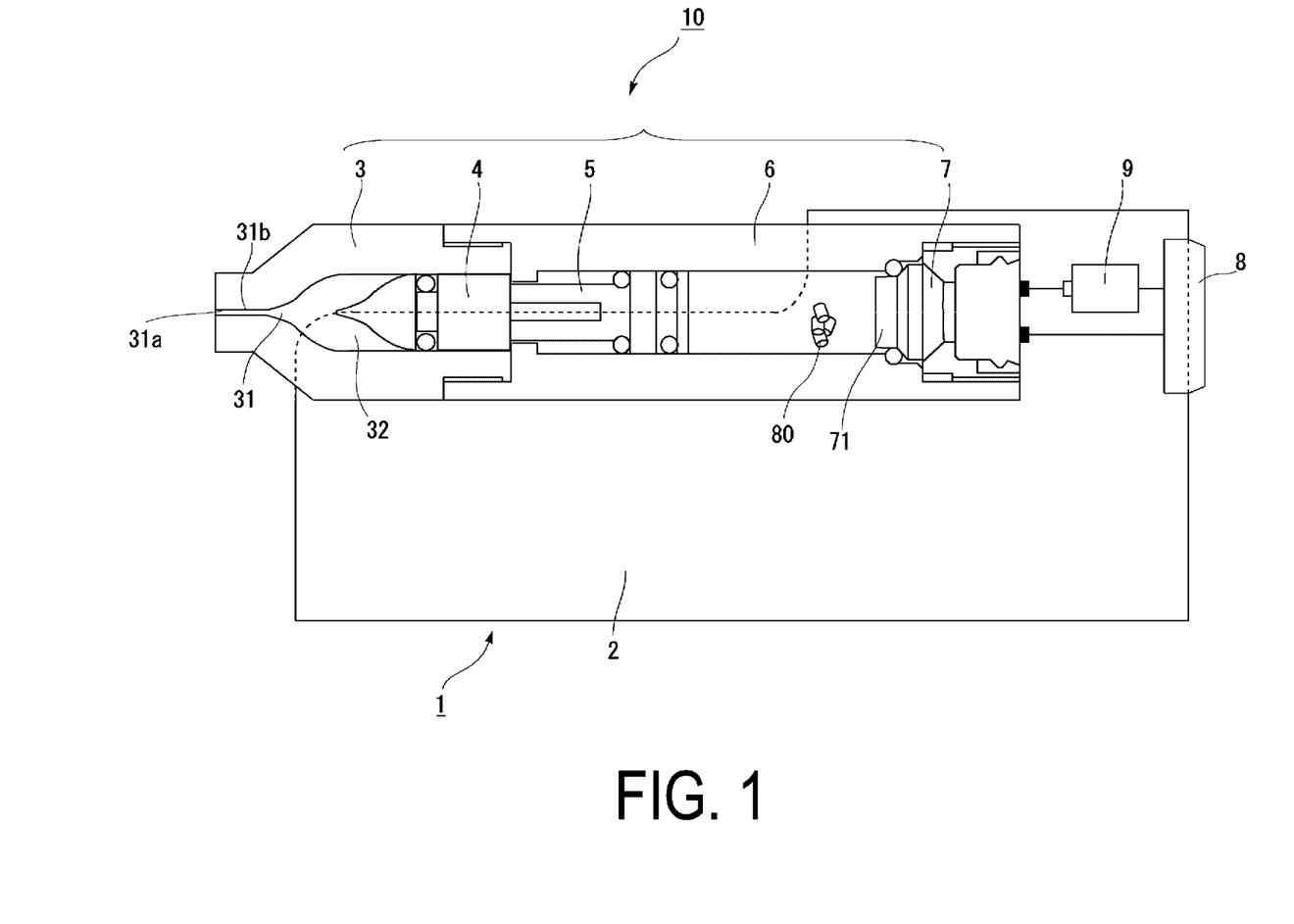
FIG. 1 is a view illustrating a schematic configuration of a needleless injector driven by an explosive.

Here, FIG. 1 is a view illustrating a schematic configuration of the injector 1 and is also a cross-sectional view of the injector 1 taken along the longitudinal direction. In the injector 1, a device assembly 10, which is obtained by integrally assembling a sub-assembly 10A (see FIG. 2A to be described later) configured by a syringe portion 3 and a plunger 4 to be described later with a sub-assembly 10B (see FIG. 2B to be described later) configured by an injector main body 6, a piston 5, and the drive portion 7, is attached to an injector housing 2. Note that, in the following description of the present application, the injection fluid administered to the target region by the injector 1 is formed of a liquid medium including a predetermined substance that exerts an expected effect or function in the target region. In the injection fluid, the predetermined substance may be in a state of being dissolved in the liquid that is the medium, or may be in a state of simply being mixed rather than being dissolved.

Examples of the predetermined substance included in the injection fluid include: an organism-derived substance or a substance that deploys a desired physiological activity that can be injected into the target region that is an organism. Examples of the organism-derived substance include DNA, RNA, a nucleic acid, an antibody, and a cell. Examples of the substance deploying the desired physiological activity include various substances exerting pharmacological or therapeutic effects, such as a small molecule drug, an inorganic substance such as metal particles for thermotherapy or radiotherapy, and a carrier. Further, it is sufficient that the liquid that is the medium of the injection fluid be a substance suitable for administering the predetermined substance above to the target region, and may be either aqueous or oleaginous. Further, a viscosity of the liquid that is the medium is not particularly limited, as long as the predetermined substance can be injected by the injector 1.

The device assembly 10 is freely attachable to and detachable from the injector housing 2. A containing portion 32 (see FIG. 2A) formed between the syringe portion 3 and the plunger 4 included in the device assembly 10 is filled with the injection fluid at a preparatory stage before operation of the injector 1, and the device assembly 10 is a unit that is replaced each time the injection fluid is injected. On the other hand, a battery 9 that supplies power to an igniter 71 included in the drive portion 7 of the device assembly 10 is included on the injector housing 2 side. As a result of a user performing an operation of pressing a button 8 provided on the injector housing 2, the power from the battery 9 is supplied between an electrode on the injector housing 2 side and an electrode on the drive portion 7 side of the device assembly 10, via a wiring line. Note that the shapes and positions of the electrode on the injector housing 2 side and the electrode on the drive portion 7 side of the device assembly 10 are designed such that both the electrodes automatically come into contact with each other when the device assembly 10 is attached to the injector housing 2. Further, the injector housing 2 is a unit that can be repeatedly used as long as there is power remaining, in the battery 9, that can be supplied to the drive portion 7. Then, in the injector housing 2, when the power of the battery 9 is exhausted, the injector housing 2 may be continuously used by replacing only the battery 9.

Here, with reference to FIG. 2A and FIG. 2B, configurations of the sub-assemblies 10A and 10B, and detailed configurations of the syringe portion 3, the plunger 4, the piston 5, the injector main body 6, and the drive portion 7 included in both the sub-assemblies will be described. The syringe portion 3 includes a nozzle portion 31 including the containing portion 32 that is a space capable of storing the injection fluid, and at the same time, the plunger 4 is disposed in the sub-assembly 10A in a manner in which the plunger 4 is slidable inside the containing portion 32. The nozzle portion 31 has a columnar outer circumference on the distal end side.

For a body 30 of the syringe portion 3, nylon 6-12, polyarylate, polybutylene terephthalate, polyphenylene sulphide, a liquid crystal polymer, or the like, which are publicly known, may be used. Further, a filler such as glass fibers and glass filler may be contained in those resins. 20 to 80 mass % of glass fibers may be contained in polybutylene terephthalate, 20 to 80 mass % of glass fibers may be contained in polyphenylene sulphide, or 20 to 80 mass % of minerals may be contained in a liquid crystal polymer.

Then, in the containing portion 32 formed inside the body 30, the plunger 4 is disposed so as to be slidable in the nozzle portion 31 direction (the distal end side direction). A space formed between the plunger 4 and the body of the syringe portion 3 is a space where an injection fluid 320 is encapsulated. Note that the injection fluid 320 is transferred to the containing portion 32 using the adapter 90 illustrated in FIG. 3 and the like, and details thereof will be described later. Here, as a result of the plunger 4 sliding in the containing portion 32, the injection fluid 320 contained in the containing portion 32 is pressed and is injected by the injection port 31a after passing through an injection nozzle 31b provided on the distal end side of the nozzle portion 31. The injection port 31a is open at an end surface (distal end surface) 31c on the distal end side of the nozzle portion 31. Note that the distal end surface 31c is substantially planar apart from the injection port 31a.

The plunger 4 is formed of a material that slides smoothly inside the containing portion 32 and that does not allow the injection fluid 320 to leak from the plunger 4 side. Specific examples of the material of the plunger 4 include butyl rubber and silicon rubber. Further, there may be exemplified a styrene-based elastomer or a hydrogenated styrene-based elastomer, or a substance obtained by mixing a styrene-based elastomer or a hydrogenated styrene-based elastomer with polyolefin such as polyethylene, polypropylene, polybutene, and an α-olefin copolymer, oil such as liquid paraffin and process oil, or a powder inorganic substance such as talc, cast, and mica. Further, as the material of the plunger 4, there may be employed a polyvinyl chloride-based elastomer, an olefin-based elastomer, a polyester-based elastomer, a polyamide-based elastomer, a polyurethane-based elastomer, various rubber materials (particularly, a vulcanized material) such as natural rubber, isoprene rubber, chloroprene rubber, nitrile butadiene rubber, and styrene butadiene rubber, or a mixture thereof. Further, for the purpose of securing and adjusting sliding between the plunger 4 and the syringe portion 3, the surface of the plunger 4 and the surface of the containing portion 32 of the syringe portion 3 may be coated with various substances and subjected to surface finishing. Examples of the coating agent include polytetrafluoroethylene (PTFE), silicon oil, diamond-like carbon, nano diamonds, and the like.

Figure 2A:
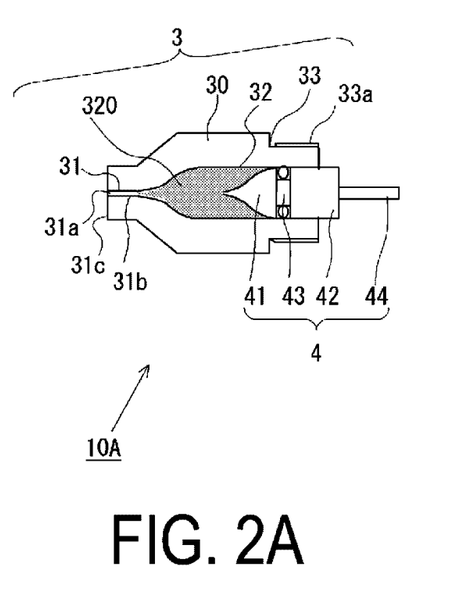
FIG. 2A is a view illustrating a schematic configuration of a first sub-assembly that forms a device assembly incorporated in the needleless injector illustrated in FIG. 1.

Here, as illustrated in FIG. 2A, the plunger 4 includes a head portion 41 and a barrel portion 42, which can be coupled by a neck portion 43 therebetween, having a diameter smaller than a diameter of the head portion 41 and the barrel portion 42. The neck portion 43 has the small diameter in this manner, and thus, an accommodating space for an O-ring, which is a seal member, is formed. Note that a contour of the head portion 41 on the distal end side has a shape that substantially matches a contour of an inner wall surface of the nozzle portion 31. In this way, when injecting the injection fluid, when the plunger 4 slides to the nozzle portion 31 side and reaches a deepest position located furthest into the containing portion 32, the space formed between the plunger 4 and the inner wall surface of the nozzle portion 31 can be reduced as much as possible, and the injection fluid 320 can thus be inhibited from remaining in the containing portion 32 and being wasted. However, the shape of the plunger 4 is not limited to a particular shape as long as desired effects can be obtained in the injector according to the present embodiment.

Furthermore, a rod portion 44, which extends from an end surface of the barrel portion 42 on the base end side in a direction further to the base end side, is provided on the plunger 4. This rod portion 44 has a diameter sufficiently smaller than that of the barrel portion 42, and the diameter is of a size enabling the user to grip the rod portion 44 and move the rod portion 44 inside the containing portion 32. When transferring the injection fluid to the containing portion 32, the user grips the rod portion 44 and moves the plunger 4, and thus draws the injection fluid from the outside into the containing portion 32. Further, a length of the rod portion 44 is determined such that, even when the plunger 4 is at the deepest position in the containing portion 32 of the syringe portion 3, the rod portion 44 protrudes from an end surface of the syringe portion 3 on the base end side, and the user can grip the rod portion 44.

Here, the description returns to the syringe portion 3. The inner diameter of the injection nozzle 31b provided in the nozzle portion 31 on the syringe portion 3 side is formed to be narrower than the inner diameter of the containing portion 32. With this type of configuration, the injection fluid 320 that is pressurized to a high pressure is ejected to the outside through the injection port 31a of the injection nozzle 31b. Further, a screw portion 33a that couples the injector main body 6 on the sub-assembly 10B side (to be described later) to the syringe portion 3 is formed on a neck portion 33 positioned on the base end side of the syringe portion 3. The diameter of the neck portion 33 is set to be smaller than the diameter of the body 30.

Next, with reference to FIG. 2B, the sub-assembly 10B including the piston 5, the injector main body 6, and the drive portion 7 will be described. Pressure is applied to the piston 5 by products of combustion generated by the igniter 71 of the drive portion 7, and the piston 5 is configured to slide inside a through-hole 64 formed inside a body 60 of the injector main body 6. Here, a coupling recess 61 is formed in the distal end side of the injector main body 6, with the through-hole 64 as a reference. The coupling recess 61 is a part that is coupled with the neck portion 33 of the syringe portion 3 described above, and a screw portion 62a, which is screwed together with the screw portion 33a provided on the neck portion 33, is formed in a side wall surface 62 of the coupling recess 61. Further, the through-hole 64 and the coupling recess 61 are communicated with each other by a communication portion 63, and the diameter of the communication portion 63 is set to be smaller than the diameter of the through-hole 64. Further, a drive portion recess 65 is formed in the base end side of the injector main body 6, with the through-hole 64 as a reference. The drive portion 7 is disposed in the drive portion recess 65.

Further, the piston 5 is formed of metal, and includes a first barrel portion 51 and a second barrel portion 52. The piston 5 is disposed in the through-hole 64, with the first barrel portion 51 being oriented to the coupling recess 61 side, and the second barrel portion 52 being oriented to the drive portion recess 65 side. The piston 5 slides inside the through-hole 64 in a state where the first barrel portion 51 and the second barrel portion 52 face an inner wall surface of the through-hole 64 of the injector main body 6. Note that, between the first barrel portion 51 and the second barrel portion 52, coupled is a coupling portion being narrower than the diameter of each of the barrel portions, and an O-ring or the like that improves adhesiveness with the inner wall surface of the through-hole 64 is disposed in a resultant space formed between both the barrel portions. Further, the piston 5 may be formed of a resin, and in this case, metal may also be used in parts for which heat resistance and pressure resistance are required.

Here, a pressing pillar portion 53 is provided on an end surface of the first barrel portion 51 on the distal end side. The diameter of the pressing pillar portion 53 is smaller than the diameter of the first barrel portion 51 and is smaller than the diameter of the communication portion 63 of the injector main body 6. An accommodation hole 54 is open in an end surface of the pressing pillar portion 53 on the distal end side. The diameter of the accommodation hole 54 is equal to or larger than the diameter of the rod portion 44, and the depth thereof is greater than a length of the rod portion 44. Thus, when the pressure is applied to the piston 5 by the products of combustion generated by the igniter 71, the pressing pillar portion 53, via the end surface on the distal end side thereof, can transmit the combustion energy thereof to the end surface on the base end side of the barrel portion 42 of the plunger 4. Note that, the shape of the piston 5 is not limited to the shape described in FIG. 2B.

Next, the drive portion 7 will be described. A body 72 of the drive portion 7 is formed in a tubular shape, and the igniter 71 is provided therein as an electric igniter that causes an ignition charge to combust and generates the energy for the injection. The drive portion 7 is disposed in the drive portion recess 65, as described above, and transmits the combustion energy generated by the igniter 71 to the second barrel portion 52 of the piston 5. Specifically, the body 72 of the drive portion 7 may be obtained by fixing an injection molded resin to a metal collar. The injection molding may be performed by a publicly known method. As the resin material for the body 72 of the drive portion 7, the same resin material as the body 30 of the syringe portion 3 may be employed.

Here, the combustion energy used in the igniter 71 for the ignition charge is the energy for the injector 1 to inject the injection fluid into the target region. Note that, examples of the ignition charge include an explosive containing zirconium and potassium perchlorate (ZPP), an explosive containing titanium hydride and potassium perchlorate (THPP), an explosive containing titanium and potassium perchlorate (TiPP), an explosive containing aluminum and potassium perchlorate (APP), an explosive containing aluminum and bismuth oxide (ABO), an explosive containing aluminum and molybdenum oxide (AMO), an explosive containing aluminum and copper oxide (ACO), an explosive containing aluminum and iron oxide (AFO), or an explosive composed of a combination of a plurality of these explosives. These explosives exhibit characteristics that, although the explosives generate high-temperature and high-pressure plasma during combustion immediately after ignition, when the products of combustion condenses at room temperature, the explosives do not contain gaseous components and hence the pressure generated decreases abruptly. An explosive other than these may be used as the ignition charge as long as appropriate injection of the injection fluid can be performed.

Further, in addition to the above-described ignition charge, a gas generating agent 80, which is combusted by the products of combustion generated by the explosive combustion at the igniter 71 and generates gas, is disposed in the injector 1, and thus a change in pressure applied to the injection fluid via the piston 5 is adjusted. A location at which the gas generating agent 80 is disposed is, for example, a location that can be exposed to the products of combustion from the igniter 71, as illustrated in FIG. 1 and FIG. 2B. Further, as another method, the gas generating agent 80 may be disposed in the igniter 71 as disclosed in WO 01-031282, JP 2003-25950 A, and the like. As an example of the gas generating agent, a single base smokeless explosive formed of 98 mass % of nitrocellulose, 0.8 mass % of diphenylamine, and 1.2 mass % of potassium sulfate can be used. Further, various types of gas generating agents used in a gas generator for an air bag and a gas generator for a seat belt pretensioner may be used. A combustion completion time of the gas generating agent can be changed by adjusting a dimension, a size, a shape, and particularly, a surface shape of the gas generating agent when disposed in the through-hole 64. In this way, the change in the pressure applied to the injection fluid can be adjusted, and a desired injection pressure transition can be obtained.

Figure 3:
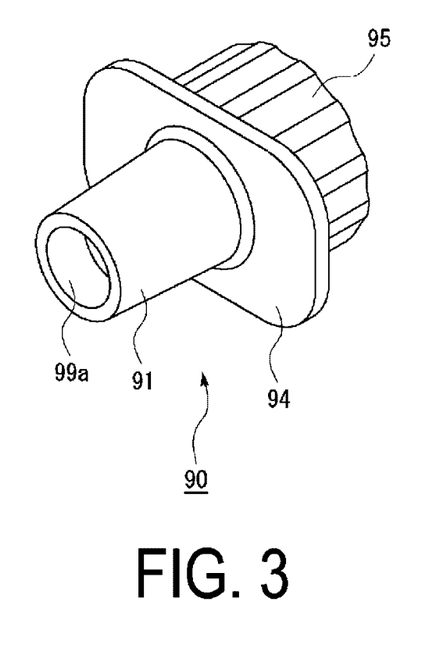
FIG. 3 is a perspective view of an adapter used to transfer, to the first sub-assembly illustrated in FIG. 2A, an injection fluid to be injected by a needleless injector.

Note that the transfer of the injection fluid 320 to the sub-assembly 10A is performed using the adapter 90 illustrated in FIG. 3. Then, in a state where the transfer of the injection fluid 320 is completed in the sub-assembly 10A, the plunger 4 is pulled out until the end surface on the base end side of the barrel portion 42 of the plunger 4 reaches a position slightly protruding from the end surface on the base end side of the syringe portion 3, as illustrated in FIG. 2A, for example.

Figure 2B:
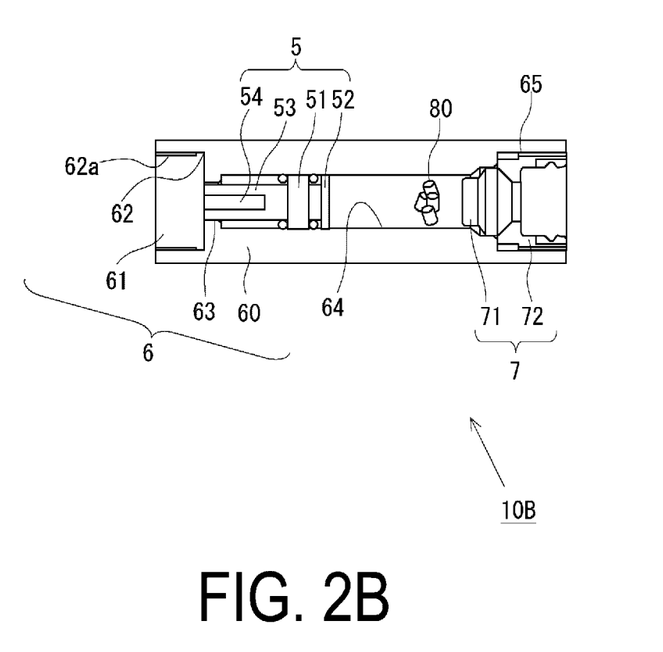
FIG. 2B is a view illustrating a schematic configuration of a second sub-assembly that forms the device assembly incorporated in the injector illustrated in FIG. 1.

Further, in the sub-assembly 10B, first, the piston 5 is inserted from the base end side of the injector main body 6 illustrated in FIG. 2B. At this time, the piston 5 is inserted into the through-hole 64, and the pressing pillar portion 53 is oriented toward the coupling recess 61 side. Then, the position of an end surface on the distal end side of the piston 5, that is, an end surface on the distal end side of the pressing pillar portion 53 in which the accommodation hole 54 is open is determined such that it protrudes by a predetermined amount from a bottom surface of the coupling recess 61 (a surface orthogonal to the side wall surface 62). When determining the position of the piston 5, a known technique, such as setting a mark for positioning in the through-hole 64 or using a jig for positioning may be employed as appropriate. Then, the gas generating agent 80 is disposed in the through-hole 64, and the drive portion 7 is attached to the drive portion recess 65. Note that a fixing force of the piston 5 in the through hole 64 is set to an extent that the piston 5 can slide through the inside of the through-hole 64 in a sufficiently smooth manner as a result of the pressure received from the products of combustion caused by the igniter 71 of the drive portion 7, and to an extent that, when attaching the sub-assembly 10A to the sub-assembly 10B, the piston 5 sufficiently resists a force received from the plunger 4, and the position of the piston 5 does not change.

The sub-assembly 10A having such a configuration is attached to the sub-assembly 10B by screwing together the screw portions 33a and 62a, and the device assembly 10 is thus formed. In this state, as the coupling of both the sub-assemblies progresses, the rod portion 44 of the plunger 4 advances and is accommodated in the accommodation hole 54 provided in the pressing pillar portion 53 of the piston 5. Finally, the end surface on the distal end side of the pressing pillar portion 53 is in a state of being in contact with the end surface on the base end side of the barrel portion 42 of the plunger 4. Note that the accommodation hole 54 has a size large enough to accommodate the rod portion 44, and thus, in this contact state, a deep inner wall surface of the accommodation hole 54 (in particular, a bottom surface of the accommodation hole 54) is not in contact with the base end side end of the rod portion 44. Therefore, the rod portion 44 does not receive a load from the piston 5 side. Furthermore, as the screwing together progresses to a final position, the position of the piston 5 is fixed in the through-hole 64 with a sufficient frictional force, as described above, and thus, the plunger 4 is pressed by the pressing pillar portion 53 and advances to the injection port 31a side, and the position of the plunger 4 is determined inside the syringe portion 3. Note that some of the injection fluid 320, which corresponds to an extrusion amount of the plunger 4, is ejected from the injection port 31a.

When the plunger 4 is positioned at the final position in this way, the formation of the device assembly 10 is complete. In the device assembly 10, the piston 5 is positioned in a predetermined position with respect to the injector main body 6. Using the piston 5 as a reference, the position of the plunger 4 in the containing portion 32 of the syringe portion 3 is mechanically and finally determined. The final position of the plunger 4 is a position that is definitively determined in the device assembly 10, and thus an amount of the injection fluid 320 that is finally contained in the containing portion 32 can be a predetermined amount that is decided in advance.

Then, the device assembly 10 is attached to the injector housing 2, and the user presses the button 8 in a state where the injection port 31a is caused to be in contact with the target region. In this way, the injection fluid 320 is pressurized via the piston 5 and the plunger 4, the injection is performed, and thus, the injection fluid 320 is injected into the target region.

Transfer of Injection Fluid to Containing Portion 32

As described above, before actuating injector 1, the user needs to assemble the sub-assembly 10A and the sub-assembly 10B, and in particular, in the assembly of the sub-assembly 10A, the user needs to transfer the injection fluid from outside to the initially empty containing portion 32. In the present embodiment, the adapter 90 illustrated in FIG. 3 is used in the transfer of the injection fluid. The transfer of the injection fluid using the adapter 90 will be described in detail below.

Figure 5:
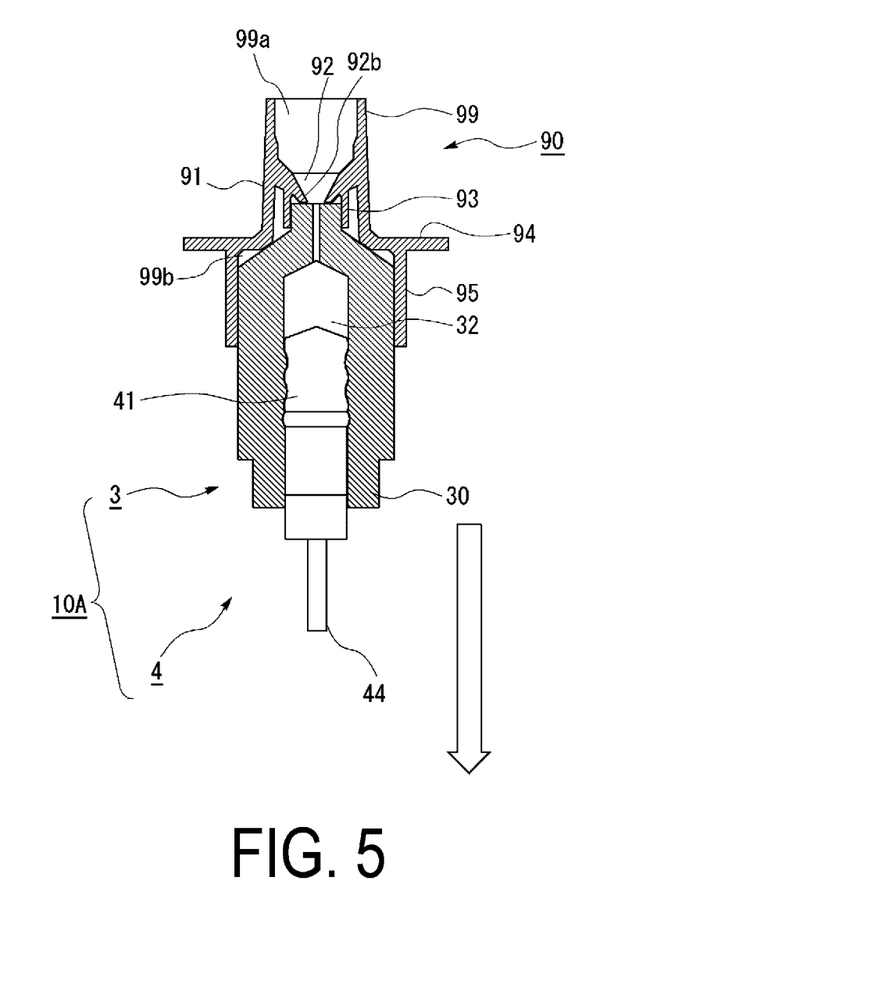
FIG. 5 is a first view illustrating a state where the adapter is attached to the first sub-assembly.

First, a configuration of the adapter 90 will be described based on FIG. 3 to FIG. 5. FIG. 3 is a perspective view of the adapter 90 and FIG. 4 is a cross-sectional view of the adapter 90. Further, FIG. 5 is a view illustrating the adapter 90 in use, and when the injection fluid is transferred to the sub-assembly 10A of the injector 1 using the adapter 90, a state is obtained where the adapter 90 is attached to the sub-assembly 10A.

The adapter 90 includes a housing 99 that forms the main body thereof. The housing 99 is formed from a predetermined resin material that is injection molded. The injection molding can be performed by a known method. The resin material of the adapter 90 is the same resin material as that of the body 30 of the syringe portion 3, and, for example, nylon 6-12, polyarylate, polybutylene terephthalate, polyphenylene sulphide, a liquid crystal polymer, or the like, which are known, can be used. Note that, for suitable flexibility to be imparted to a protruding portion 92b included in the adapter 90, as to be described below, in terms of the hardness of the resin material, compared to the body 30 of the syringe portion 3, a material having a lower hardness, based on a predetermined parameter (Vickers hardness, for example) can be employed. Alternatively, the material of the protruding portion 92b may be different from the material of the housing 99. For example, polypropylene can be used as the material of the housing 99, and silicon rubber can be used as the material of the protruding portion 92b.

The housing 99 includes an upper peripheral wall portion 91 positioned on the upper side in a state illustrated in FIG. 4, a flange portion 94 coupled to the upper peripheral wall portion 91, and a lower peripheral wall portion 95 coupled to the flange portion 94 and positioned below the flange portion 94. As illustrated in FIG. 3, the upper peripheral wall portion 91, the flange portion 94, and the lower peripheral wall portion 95 are portions that are visible from the outside of the adapter 90. Then, the upper peripheral wall portion 91 has a substantially cylindrical shape that is coupled to the flange portion 94 in a state where the upper peripheral wall portion 91 is tapered more toward a center axis L1 of the adapter 90 as going upward from the flange portion 94. As a result, a predetermined space 99a inside the housing 99 is defined by the upper peripheral wall portion 91. This predetermined space 99a functions as the containing portion 99a in which the injection fluid is contained. As described below, the containing portion 99a is connected to a filling nozzle 92 in a lower portion thereof, and the containing portion 99a is formed in a manner in which the inner diameter of a partial region R1 of the lower portion of the containing portion 99a including the connected portion therewith becomes smaller the further downward from the top to the bottom (toward the filling nozzle 92 side).

Furthermore, inside the upper peripheral wall portion 91, the filling nozzle 92 is provided that is positioned below the containing portion 99a and that is in communication with the containing portion 99a. The filling nozzle 92 includes a protruding portion formed by a portion of the inner wall surface of the upper peripheral wall portion 91 protruding in a ring shape toward the distal end side of the adapter 90 while narrowing the internal space thereof. As a result, the uppermost end (the base end) of the filling nozzle 92 is in communication with the containing portion 99a, and the inner diameter of the filling nozzle 92 at the uppermost end thereof matches the inner diameter of the lowermost end of the containing portion 99a connected thereto. On the other hand, an open end 92a is formed at the lowermost end (the distal end) of the filling nozzle 92, that is, the distal end portion of the protruding portion, and the inner diameter of the open end 92a is set to be smaller than the inner diameter of the containing portion 99a, in particular, smaller than the inner diameter of the above-described lowermost end of the containing portion 99a at which the inner diameter is smallest. Then, in the filling nozzle 92, the filling nozzle 92 is formed in a manner in which the inner diameter thereof becomes smaller the further from the uppermost end to the open end 92a, which is the lowermost end thereof. In this manner, in the internal space of the filling nozzle 92, a flow path into which the injection fluid contained in the containing portion 99a flows is formed, and the injection fluid can move further downward inside the housing 99 through the open end 92a.

Further, a tubular cylindrical portion 93 is provided extending downward from partway on the slope of the outer periphery of the filling nozzle 92. An inner wall surface 93a of the cylindrical portion 93 is substantially parallel to the center axis L1 of the adapter 90. The cylindrical portion 93 corresponds to a first cylindrical portion. The inner diameter of the internal space defined by the inner wall surface 93a corresponds to, and preferably substantially matches, the outer diameter of the columnar nozzle portion 31 positioned at the distal end portion of the body 30 of the syringe portion 3 (the portion positioned furthest to the left side in the state illustrated in FIG. 2A). Then, in the filling nozzle 92, a portion, from a position at which the cylindrical portion 93 is provided, to the distal end portion of the filling nozzle 92, is the protruding portion 92b. The protruding portion 92b is formed in a state of protruding in an annular shape in the internal space of the cylindrical portion 93, and the open end 92a of the filling nozzle 92 is defined by an end edge on the distal end side of the protruding portion 92b. The length of the protruding portion 92b (or the height in the direction along the center axis L1) is of an extent that the open end 92a is sufficiently accommodated in the internal space of the cylindrical portion 93, in other words, is of an extent that secures a state where the cylindrical portion 93 extends sufficiently downward from the distal end portion of the protruding portion 92b.

Next, the flange portion 94 is connected at the lowermost end portion of the upper peripheral wall portion 91 and is a planar member orthogonal to the center axis L1, as illustrated in FIG. 4. Further, the lower peripheral wall portion 95 is a cylindrical member provided orthogonal to the flange portion 94, and an inner wall surface 95a thereof is substantially parallel to the center axis L1 of the adapter 90. The lower peripheral wall portion 95 corresponds to a second cylindrical portion. The inner diameter of the internal space defined by the inner wall surface 95a corresponds to, and preferably substantially matches, the outer diameter of a middle portion of the body 30 of the syringe portion 3 (in the state illustrated in FIG. 2A, a portion between the distal end portion at which the nozzle portion 31 is positioned and the proximal end portion at which the screw portion 33a is provided, namely, the fattest portion in the body 30). Therefore, the inner diameter of the internal space defined by the inner wall surface 95a is larger than the inner diameter of the internal space defined by the above-described inner wall surface 93a. Further, inside the housing 99, the internal space defined by the inner wall surface 95a is in communication with the internal space defined by the upper peripheral wall portion 91. However, the cylindrical portion 93 does not reach the internal space defined by the inner wall surface 95a.

In the transfer of the injection fluid, the adapter 90 configured in this manner is attached to the sub-assembly 10A in a manner in which the adapter 90 is positioned above the sub-assembly 10A, as illustrated in FIG. 5. This attached state will be described based on FIG. 5. When attaching the adapter 90, the injection port 31a of the sub-assembly 10A is preferably disposed facing upward (in the vertical direction). Note that the injection port 31a need not necessarily face upward, but when transferring the injection fluid as described below, since the rod portion 44 is operated in a state where the injection fluid is contained in the containing portion 99a, the injection port 31a preferably faces upward as much as possible so that the injection fluid does not leak. Further, immediately after the adapter 90 is attached to the sub-assembly 10A, taking into account a subsequent operation of the rod portion 44, the head portion 41 of the plunger 4 is caused to be in a state of being in contact with the end surface positioned innermost in the containing portion 32.

With respect to this type of the sub-assembly 10A, the distal end portion of the body 30 is inserted into the internal space of the lower peripheral wall portion 95 of the adapter 90, a state is obtained where the inner wall surface 95a of the lower peripheral wall portion 95 is fitted with the middle portion of the body 30, and a state is obtained where the inner wall surface 93a of the cylindrical portion 93 is fitted with the columnar distal end portion of the body 30. Then, while maintaining these fitted states, the sub-assembly 10A is inserted into the adapter 90 until the distal end portion of the protruding portion 92b comes into contact with the distal end surface 31c of the nozzle portion 31. Note that the attached state illustrated in FIG. 5 illustrates the state where the distal end portion of the protruding portion 92b is in contact with the distal end surface 31c of the nozzle portion 31.

In this attached state, the injection port 31a of the nozzle portion 31 and the open end 92a of the filling nozzle 92 are in an overlapping state. As a result, a state is obtained where the injection fluid contained in the containing portion 99a can flow to the nozzle portion 31 side of the sub-assembly 10A, via the open end 92a and the injection port 31a. Note that in this state, since the open end 92a is larger than the injection port 31a, the annular protruding portion 92b is in contact with the distal end surface 31c in an annular shape surrounding the injection port 31a without blocking the injection port 31a. Furthermore, as described above, the housing 99 including the protruding portion 92b is formed from a resin material that can exhibit suitable flexibility, and thus, when the protruding portion 92b is abutted against the distal end surface 31c as a result of the user's operation when the adapter 90 is attached, the protruding portion 92b deflects in a suitable manner, and a favorable contact state is formed between the protruding portion 92b and the distal end surface 31c. As a result, a favorable sealing performance is created between the protruding portion 92b and the distal end surface 31c, and when pouring the injection fluid into the containing portion 99a, wasteful leakage of the injection fluid can be suppressed.

In this way, in the attached state illustrated in FIG. 5, the protruding portion 92b is in the state of being in contact with the distal end surface 31c in an annular shape, and a state is obtained where the adapter 90 is supported in a stable manner with respect to the sub-assembly 10A, by the cylindrical portion 93 and the lower peripheral wall portion 95. Thus, the safe transfer of the injection fluid can be achieved.

Figure 6:
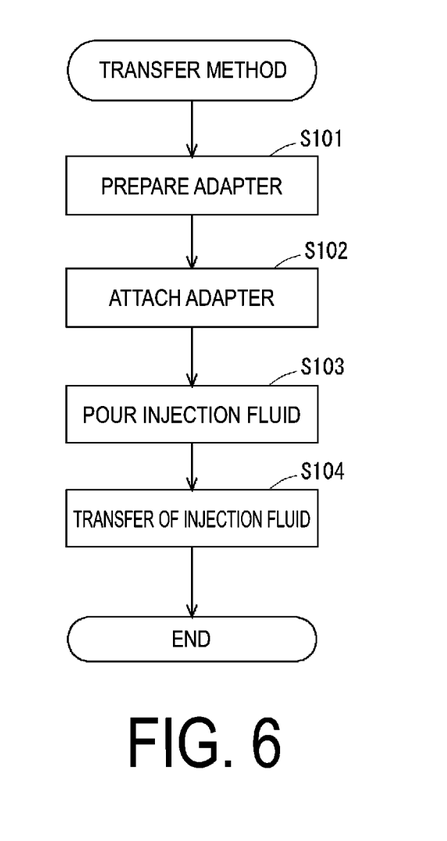
FIG. 6 is a flowchart illustrating a flow of a transfer method of the injection fluid, using the adapter.

The actual transfer of the injection fluid transfer is performed in accordance with a flow illustrated in FIG. 6. First, the above-described adapter 90 is prepared (a process at S101). At this time, as described above, in the sub-assembly 10A, the head portion 41 of the plunger 4 is in contact with the end surface positioned innermost in the containing portion 32. Next, the adapter 90 is attached to the sub-assembly 10A constituting the injector 1, thus forming the attached state illustrated in FIG. 5, as described above (a process at S102). Then, in a state where the containing portion 99a is positioned on the upper side (the state illustrated in FIG. 5), the injection fluid to be transferred from the open end of the containing portion 99a is poured into the containing portion 99a.

When the pouring of the injection fluid into the containing portion 99a is complete, the rod portion 44 is pulled downward by the user while maintaining the state where the containing portion 99a is positioned on the upper side so that the injection fluid does not leak. In accordance with the movement of the rod portion 44, the injection fluid in the containing portion 99a flows into the injection nozzle 31b via the injection port 31a, and the transfer is performed until the injection fluid reaches the containing portion 32. Here, in the adapter 90, attention will be directed to the entire space inside the housing portion 99a including the partial region R1 and the filling nozzle 92. These spaces (regions) form a space inside the adapter 90 that is continuous from the partial region R1 to the open end 92a, and this space corresponds to a predetermined space. Then, this continuous space is configured in a manner in which the inner diameter of the continuous space decreases from the upper side of the adapter 90 to the open end 92a.

In such a configuration, in the internal space of the adapter 90, the inner wall surface thereof is continuously inclined with respect to the center axis L1, and the internal space gradually becomes narrower. When suction force generated by the rod portion 44 being pulled downward acts on the injection fluid, due to the presence of this continuously inclined surface, the injection fluid is less likely to be dispersed inside the filling nozzle 92 and is more easily collected with respect to the injection port 31a. In particular, when an amount of the injection fluid to be transferred is low, the influence of a resistance force received from the inner wall surface of the filling nozzle 92 becomes large, and it becomes difficult to cause the above-described suction force to act effectively on the injection fluid. However, by forming a collection structure of the injection fluid using this type of continuous inclined surface (in other words, for example, a funnel-shaped structure), as well as the efficient transfer of the injection fluid, at the time of the transfer, it is possible to perform the transfer while suppressing an extent to which air present in the surroundings become mixed with the injection fluid. Note that, as described above, the above-described continuous inclined surface is more preferably formed in all of the space inside the filling nozzle 92, but, as long as the mixing of the injection fluid and the air is caused to be unlikely to occur, a space defined by an inner wall surface other than the above-described inclined surface (for example, an inner wall surface parallel to the center axis L1) may be included as part of the internal space of the filling nozzle 92.

Further, as described above, since the open end 92a is larger than the injection port 31a, when the rod portion 44 is lowered by being pulled downward, the injection fluid easily flows relatively smoothly in the filling nozzle 92. Furthermore, since the annular protruding portion 92b is in contact with the distal end surface 31c with a high sealing performance, suction force resulting from the movement of the rod portion 44 can be effectively generated, and the transfer of the injection fluid can also be suitably performed from this point.

When the transfer of the injection fluid by the operation of the rod portion 44 is complete, the adapter 90 is removed from the sub-assembly 10A, and a state is obtained where the containing portion 32 is filled with the injection fluid, as illustrated in FIG. 2A. After that, by assembling the sub-assembly 10A with the sub-assembly 10B and mounting the assembly in the injector housing 2, the injector 1 in a usable state can be prepared.

Modified Example 1

In the above-described embodiment, in the attached state of the adapter 90, the attached state of the adapter with respect to the sub-assembly 10A is stabilized by obtaining the state where the inner wall surface 93a of the cylindrical portion 93 is fitted with the outer peripheral wall surface of the columnar nozzle portion 31. In the present modified example, the outer peripheral wall surface of the nozzle portion 31 may be formed as a tapered surface that is inclined along an axial direction thereof (for example, a tapered surface formed in a manner in which the outer diameter of the nozzle portion 31 becomes larger the further toward a right side in the drawing in the state illustrated in FIG. 2A (the base end side of the syringe portion 3)). By forming the tapered surface in this manner, the sub-assembly 10A is easily inserted into the adapter 90, and the inner wall surface 93a and the tapered surface are fitted while being pressed together, and thus, a coupling force in the attached state can be increased and a more stable attached state can be formed.

Modified Example 2

Figure 7:
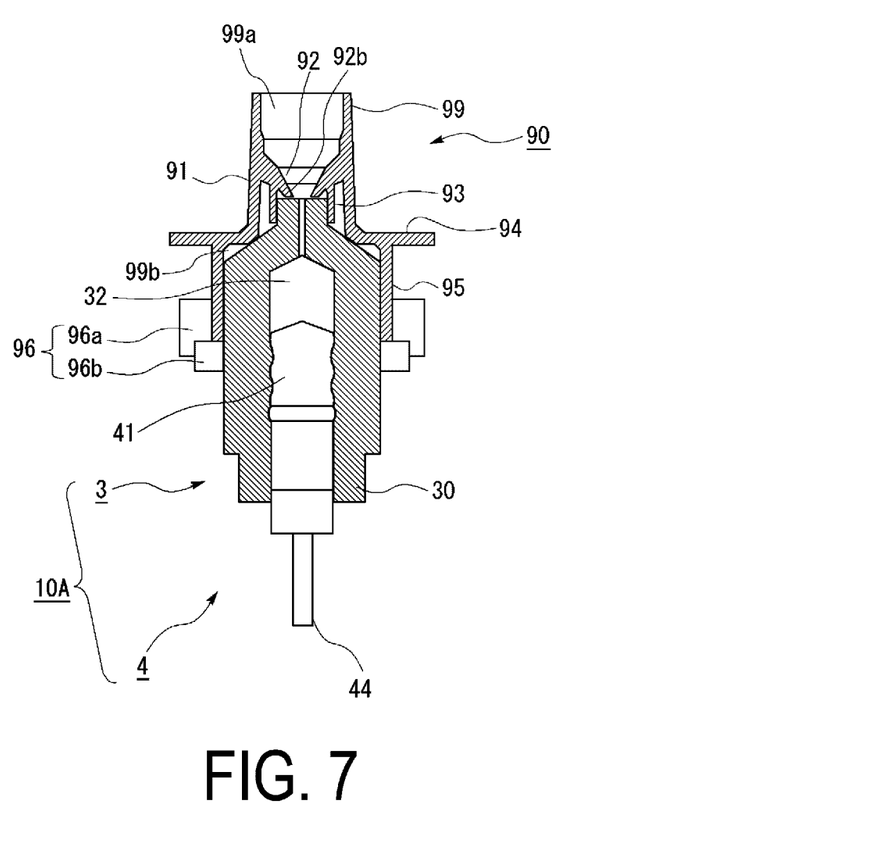
FIG. 7 is a second view illustrating a state where the adapter is attached to the first sub-assembly.

A modified example of the adapter 90 will be described based on FIG. 7. In the adapter 90 illustrated in FIG. 7, a holding device 96 is provided that holds the attached state between the adapter 90 and the sub-assembly 10A. The holding device 96 is formed of a first member 96a provided on the adapter 90 side and a second member 96b provided on the sub-assembly 10A side and holds the attached state between the adapter 90 and the sub-assembly 10A as a result of those members being mechanically coupled, or the like. Examples of the holding device 96 include, for example, a snap fit mechanism that can be engaged and released. By employing such a holding device 96, the coupling force in the attached state can be increased, and a more stable attached state can thus be maintained.

REFERENCE SIGNS LIST

1 Injector (needleless injector)
2 Injector housing
3 Syringe portion
4 Plunger
5 Piston
10 Device assembly
10A Sub-assembly
10B Sub-assembly
30 Body
31 Nozzle portion
31a Injection port
31b Injection nozzle
31c Distal end surface
32 Containing portion
44 Rod portion
90 Adapter
91 Upper peripheral wall portion
92 Filling nozzle
92a Open end
92b Protruding portion
93 Cylindrical portion
93a Inner wall surface
94 Flange portion
95 Lower peripheral wall portion
95a Inner wall surface
96 Holding device
96a First member
96b Second member
99 Housing
99a Containing portion
R1 Partial region

The invention claimed is:
1. An adapter for transferring a predetermined injection fluid, via an injection port of an injection nozzle, to an injection device that injects the predetermined injection fluid from the injection nozzle, the adapter comprising:
a housing defining a containing portion containing the predetermined injection fluid to be transferred, the housing being configured to be attachable to and detachable from the injection device; and
a filling nozzle provided in communication with the containing portion in the housing, when the housing is attached to the injection device, the filling nozzle being configured to come into contact with an end surface of the injection device, in which the injection port of the injection nozzle is formed, the filling nozzle being configured to allow the predetermined injection fluid contained in the containing portion to flow to a side of the injection nozzle, an open end of the filling nozzle being set to be smaller than an inner diameter of the containing portion and larger than the injection port of the injection nozzle,
wherein
the filling nozzle includes a protruding portion having an annular shape and protruding from the filling nozzle toward a distal end side of the adapter, the protruding portion is formed in a manner where, when the housing is attached to the injection device, a distal end of the protruding portion comes into contact with the end surface of the injection device,
wherein
of an internal space of the housing from a partial region of the containing portion to the open end of the filling nozzle, at least a predetermined space inside the protruding portion is formed in a manner where an inner diameter of the predetermined space decreases toward a side of the open end of the filling nozzle.
2. The adapter according to claim 1, wherein
the predetermined space is a space including all of the internal space of the partial region and the filling nozzle, and
from the partial region to the open end of the filling nozzle, the predetermined space is formed in a manner where the inner diameter of the predetermined space decreases continuously toward the side of the open end of the filling nozzle.
3. The adapter according to claim 1, wherein
the protruding portion is formed of a flexible member.
4. The adapter according to claim 1, wherein
the injection device includes a nozzle portion having a cylindrical shape and internally including the injection nozzle, the nozzle portion being formed exposing the injection port of the injection nozzle at an end surface of the nozzle portion, and
the housing includes a first cylindrical portion provided surrounding the filling nozzle, in the housing, the first cylindrical portion being in a fitted state with an outer peripheral wall surface of the nozzle portion when the housing is attached to the injection device.
5. The adapter according to claim 4, wherein
the outer peripheral wall surface of the nozzle portion forms a tapered surface inclined along an axial direction of the nozzle portion, and
when the housing is attached to the injection device, an inner wall surface of the first cylindrical portion is in the fitted state while pressing the outer peripheral wall surface of the nozzle portion.
6. The adapter according to claim 4, further comprising:
a holding portion configured to hold the fitted state between the first cylindrical portion and the outer peripheral wall surface of the nozzle portion when the housing is attached to the injection device.

7. The adapter according to claim 4, wherein
the housing includes a second cylindrical portion provided surrounding the first cylindrical portion, in the housing, the second cylindrical portion being in a fitted state with an outer peripheral wall surface of the injection device when the housing is attached to the injection device.

8. An injection fluid transfer method comprising:
preparing an adapter for transferring a predetermined injection fluid, via an injection port of an injection nozzle, to an injection device that injects the predetermined injection fluid from the injection nozzle, the adapter including a housing defining a containing portion containing the predetermined injection fluid to be transferred and a filling nozzle connected to the containing portion in the housing, an open end of the filling nozzle being set to be smaller than an inner diameter of the containing portion and larger than the injection port of the injection nozzle, the filling nozzle including a protruding portion having an annular shape and protruding from the filling nozzle toward a distal end side of the adapter, the protruding portion being formed in a manner where, when the housing is attached to the injection device, a distal end of the protruding portion comes into contact with the end surface of the injection device, of an internal space of the housing from a partial region of the containing portion connected to the filling nozzle to the open end of the filling nozzle, at least a predetermined space inside the protruding portion being formed in a manner where an inner diameter of the predetermined space decreases toward a side of the open end of the filling nozzle;
attaching the housing to the injection device and causing a distal end of the filling nozzle to be in contact with an end surface of the injection device, in which the injection port of the injection nozzle is formed;
pouring the predetermined injection fluid into the containing portion; and
transferring the predetermined injection fluid from the containing portion to the injection device in a state where the adapter is positioned above the injection device in a vertical direction.

* * * * *